United States Patent
Rusin

(10) Patent No.: US 11,207,129 B2
(45) Date of Patent: *Dec. 28, 2021

(54) ELECTRIC STAPLER DEVICE

(71) Applicant: Covidien LP, Mansfield, MA (US)

(72) Inventor: Christopher T. Rusin, Golden, CO (US)

(73) Assignee: Covidien LP, Mansfield, MA (US)

( * ) Notice: Subject to any disclaimer, the term of this patent is extended or adjusted under 35 U.S.C. 154(b) by 40 days.

This patent is subject to a terminal disclaimer.

(21) Appl. No.: 16/781,354

(22) Filed: Feb. 4, 2020

(65) Prior Publication Data

US 2020/0170700 A1 Jun. 4, 2020

Related U.S. Application Data

(63) Continuation of application No. 15/367,868, filed on Dec. 2, 2016, now Pat. No. 10,548,658, which is a
(Continued)

(51) Int. Cl.
*A61B 18/14* (2006.01)
*A61B 18/00* (2006.01)
(Continued)

(52) U.S. Cl.
CPC ........ *A61B 18/1445* (2013.01); *A61B 17/072* (2013.01); *A61B 17/1155* (2013.01);
(Continued)

(58) Field of Classification Search
CPC ............ A61B 18/1442; A61B 18/1445; A61B 18/1447; A61B 2018/1442;
(Continued)

(56) References Cited

U.S. PATENT DOCUMENTS

| D249,549 S | 9/1978 | Pike |
| D263,020 S | 2/1982 | Rau, III |

(Continued)

FOREIGN PATENT DOCUMENTS

| CN | 201299462 Y | 9/2009 |
| DE | 2415263 A1 | 10/1975 |

(Continued)

OTHER PUBLICATIONS

Michael Choti, "Abdominoperineal Resection with the LigaSure Vessel Sealing System and LigaSure Atlas 20 cm Open Instrument" Innovations That Work, Jun. 2003.

(Continued)

*Primary Examiner* — Linda C Dvorak
*Assistant Examiner* — Annabeth E Rodriguez
(74) *Attorney, Agent, or Firm* — Carter, DeLuca & Farrell LLP

(57) ABSTRACT

An end effector assembly adapted to couple to an electrosurgical instrument, the end effector assembly including a plurality of spaced apart small seal plates on opposing jaw members where each seal plate forms a pair of seal plates with the corresponding seal plate on the opposing jaw member. Each pair of seal plates is individually activatable, and the pair of seal plates are activated in sequence. When the opposing jaw members are in an approximated position, the pairs of seal plates around the periphery of each jaw member define a gap therebetween that is larger than the gap between pairs of seal plates along the center of each jaw member.

15 Claims, 10 Drawing Sheets

Related U.S. Application Data continuation of application No. 14/043,039, filed on Oct. 1, 2013, now Pat. No. 9,526,564.

(60) Provisional application No. 61/711,063, filed on Oct. 8, 2012.

(51) Int. Cl.

| | | |
|---|---|---|
| *A61B 18/12* | (2006.01) | |
| *A61B 17/072* | (2006.01) | |
| *A61B 17/115* | (2006.01) | |
| *A61B 34/00* | (2016.01) | |
| *A61B 17/00* | (2006.01) | |
| *A61B 17/11* | (2006.01) | |

(52) U.S. Cl.
CPC .......... *A61B 18/1442* (2013.01); *A61B 34/76* (2016.02); *A61B 2017/00504* (2013.01); *A61B 2017/00893* (2013.01); *A61B 2017/07228* (2013.01); *A61B 2017/07242* (2013.01); *A61B 2017/1132* (2013.01); *A61B 2018/00011* (2013.01); *A61B 2018/0063* (2013.01); *A61B 2018/00083* (2013.01); *A61B 2018/00601* (2013.01); *A61B 2018/00607* (2013.01); *A61B 2018/00642* (2013.01); *A61B 2018/00654* (2013.01); *A61B 2018/00702* (2013.01); *A61B 2018/00827* (2013.01); *A61B 2018/00875* (2013.01); *A61B 2018/00892* (2013.01); *A61B 2018/124* (2013.01); *A61B 2018/126* (2013.01); *A61B 2018/1412* (2013.01); *A61B 2018/1455* (2013.01)

(58) Field of Classification Search
CPC ...... A61B 2018/145; A61B 2018/1452; A61B 2018/1455; A61B 2018/1457; A61B 2018/146; A61B 2018/1462
See application file for complete search history.

(56) References Cited

U.S. PATENT DOCUMENTS

| | | | |
|---|---|---|---|
| 4,354,628 A | 10/1982 | Green | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| 5,014,899 A | 5/1991 | Presty et al. | |
| 5,040,715 A | 8/1991 | Green et al. | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| 5,443,463 A | 8/1995 | Stern et al. | |
| 5,611,813 A * | 3/1997 | Lichtman ............... | A61B 17/29 606/174 |
| D384,413 S | 9/1997 | Zlock et al. | |
| H1745 H | 8/1998 | Paraschac | |
| 5,799,857 A | 9/1998 | Robertson et al. | |
| D402,028 S | 12/1998 | Grimm et al. | |
| 5,849,022 A * | 12/1998 | Sakashita ............... | A61B 17/29 606/174 |
| D408,018 S | 4/1999 | McNaughton | |
| 5,915,616 A | 6/1999 | Viola et al. | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| 6,475,179 B1 | 11/2002 | Wang et al. | |
| D493,888 S | 8/2004 | Reschke | |
| D496,997 S | 10/2004 | Dycus et al. | |
| 6,802,843 B2 | 10/2004 | Truckai et al. | |
| D499,181 S | 11/2004 | Dycus et al. | |
| D502,994 S | 3/2005 | Blake, III | |
| D509,297 S | 9/2005 | Wells | |
| 6,989,010 B2 | 1/2006 | Francischelli et al. | |
| D525,361 S | 7/2006 | Hushka | |
| 7,083,618 B2 | 8/2006 | Couture et al. | |
| 7,087,054 B2 | 8/2006 | Truckai et al. | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,455,676 B2 | 11/2008 | Holsten et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 7,877,853 B2 | 2/2011 | Unger et al. | |
| 8,028,884 B2 | 10/2011 | Sniffin et al. | |
| D649,249 S | 11/2011 | Guerra | |
| D649,643 S | 11/2011 | Allen, IV et al. | |
| D661,394 S | 6/2012 | Romero et al. | |
| 8,480,671 B2 | 7/2013 | Mueller | |
| 8,556,929 B2 | 10/2013 | Harper et al. | |
| 8,679,140 B2 | 3/2014 | Butcher | |
| RE44,834 E | 4/2014 | Dumbauld et al. | |
| 8,858,553 B2 | 10/2014 | Chojin | |
| 8,858,554 B2 | 10/2014 | Kerr et al. | |
| 8,920,461 B2 | 12/2014 | Unger et al. | |
| 8,968,298 B2 | 3/2015 | Twomey | |
| 8,968,308 B2 | 3/2015 | Horner et al. | |
| 8,968,311 B2 | 3/2015 | Allen, IV et al. | |
| 8,968,313 B2 | 3/2015 | Larson | |
| 9,011,436 B2 | 4/2015 | Garrison | |
| 9,016,541 B2 | 4/2015 | Viola et al. | |
| 9,023,039 B2 | 5/2015 | Kerr | |
| 9,034,009 B2 | 5/2015 | Twomey et al. | |
| 9,039,691 B2 | 5/2015 | Moua et al. | |
| 9,072,524 B2 | 7/2015 | Heard et al. | |
| 9,113,901 B2 | 8/2015 | Allen, IV et al. | |
| 9,113,904 B2 | 8/2015 | Kerr et al. | |
| 9,113,905 B2 | 8/2015 | McKenna et al. | |
| 9,113,906 B2 | 8/2015 | Mueller | |
| 9,237,891 B2 | 1/2016 | Shelton, IV | |
| 9,265,570 B2 | 2/2016 | Heard | |
| 9,526,564 B2 * | 12/2016 | Rusin ................... | A61B 17/072 |
| 10,548,658 B2 * | 2/2020 | Rusin ................... | A61B 17/1155 |
| 2002/0111624 A1 * | 8/2002 | Witt ................... | A61B 18/1442 606/51 |
| 2006/0079934 A1 * | 4/2006 | Ogawa ................... | A61B 17/29 606/205 |
| 2008/0041918 A1 | 2/2008 | Holsten et al. | |
| 2008/0045947 A1 * | 2/2008 | Johnson ........... | A61B 17/07207 606/51 |
| 2009/0173766 A1 | 7/2009 | Wenchell | |

(56) References Cited

U.S. PATENT DOCUMENTS

| | | |
|---|---|---|
| 2010/0100122 A1 | 4/2010 | Hinton |
| 2011/0046623 A1 | 2/2011 | Reschke |
| 2011/0193608 A1 | 8/2011 | Krapohl |
| 2012/0323238 A1 | 12/2012 | Tyrrell et al. |
| 2013/0103035 A1* | 4/2013 | Horner ............... A61B 18/1445 606/51 |
| 2013/0247343 A1 | 9/2013 | Horner et al. |
| 2013/0253489 A1 | 9/2013 | Nau, Jr. et al. |
| 2013/0255063 A1 | 10/2013 | Hart et al. |
| 2013/0267949 A1 | 10/2013 | Kerr |
| 2013/0274736 A1 | 10/2013 | Garrison |
| 2013/0289561 A1 | 10/2013 | Waaler et al. |
| 2013/0296922 A1 | 11/2013 | Allen, IV et al. |
| 2013/0304058 A1 | 11/2013 | Kendrick |
| 2013/0304066 A1 | 11/2013 | Kerr et al. |
| 2013/0310832 A1 | 11/2013 | Kerr et al. |
| 2013/0325057 A1 | 12/2013 | Larson et al. |
| 2013/0338666 A1 | 12/2013 | Bucciaglia et al. |
| 2013/0338693 A1 | 12/2013 | Kerr et al. |
| 2013/0345701 A1 | 12/2013 | Allen, IV et al. |
| 2013/0345735 A1 | 12/2013 | Mueller |
| 2014/0025052 A1 | 1/2014 | Nau, Jr. et al. |
| 2014/0025053 A1 | 1/2014 | Nau, Jr. et al. |
| 2014/0025059 A1 | 1/2014 | Kerr |
| 2014/0025066 A1 | 1/2014 | Kerr |
| 2014/0025070 A1 | 1/2014 | Kerr et al. |
| 2014/0031821 A1 | 1/2014 | Garrison |
| 2014/0046323 A1 | 2/2014 | Payne et al. |
| 2014/0066910 A1 | 3/2014 | Nau, Jr. |
| 2014/0066911 A1 | 3/2014 | Nau, Jr. |
| 2014/0074091 A1 | 3/2014 | Arya et al. |
| 2014/0100564 A1 | 4/2014 | Garrison |
| 2014/0100568 A1 | 4/2014 | Garrison |
| 2015/0230857 A1 | 8/2015 | Horner et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 102004026179 B4 | 1/2009 |
| DE | 102008018406 B3 | 7/2009 |
| EP | 1281878 A1 | 2/2003 |
| EP | 1159926 A2 | 3/2003 |
| JP | 61501068 A | 5/1986 |
| JP | 1024051 | 1/1989 |
| JP | 1147150 | 6/1989 |
| JP | 55106 | 1/1993 |
| JP | 0540112 A | 2/1993 |
| JP | 6121797 A | 5/1994 |
| JP | 6285078 A | 10/1994 |
| JP | 06343644 | 12/1994 |
| JP | 6511401 | 12/1994 |
| JP | 07265328 | 10/1995 |
| JP | 856955 | 5/1996 |
| JP | 08252263 A | 10/1996 |
| JP | 8289895 | 11/1996 |
| JP | 8317934 A | 12/1996 |
| JP | 8317936 A | 12/1996 |
| JP | 910223 A | 1/1997 |
| JP | 09000538 A | 1/1997 |
| JP | 9122138 A | 5/1997 |
| JP | 0010000195 A | 1/1998 |
| JP | 10155798 A | 6/1998 |
| JP | 1147149 | 2/1999 |
| JP | 11070124 A | 3/1999 |
| JP | 11169381 A | 6/1999 |
| JP | 11192238 A | 7/1999 |
| JP | 11244298 | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001003400 A | 1/2001 |
| JP | 2001008944 | 1/2001 |
| JP | 2001029355 | 2/2001 |
| JP | 2001029356 | 2/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2006015078 A | 1/2006 |
| JP | 2006501939 A | 1/2006 |
| JP | 2006095316 A | 4/2006 |
| JP | 2011125195 A | 6/2011 |
| JP | 0006030945 B2 | 11/2016 |
| JP | 6502328 B2 | 4/2019 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.

Peterson et al., "Comparison of Healing Process Following Ligation with Sutures and Bipolar Vessel Sealing" Surgical Technology International (2001).

"Electrosurgery: A Historical Overview" Innovations in Electrosurgery; Sales-Product Literature; Dec. 31, 2000.

Johnson et al. "Evaluation of a Bipolar Electrothermal Vessel Sealing Device in Hemorrhoidectomy" Sales/Product Literature; Jan., 2004.

E. David Crawford, "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

(56) References Cited

OTHER PUBLICATIONS

Muller et al. "Extended Left Hemicolectomy Using the LigaSure Vessel Sealing System" Innovations That Work; Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work,Jun. 2002.
Heniford et al. "Initial Research and Clinical Results with an Electrothermal Bipolar Vessel Sealer" Oct. 1999.
Heniford et al "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al., "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females". Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room"; Sales/Product Literature 2001.
Bergdahl et al., "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al., "Sutureless Closed Hemorrhoidectomy: A New Technique" Annals of Surgery, vol. 234, No. 1, Jul. 2001, pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al." Use of a New Energy-based Vessel Ligation Device During Vaginal Hysterectomy"; Int'l Federation of Gynecology and Obstetrics (FIGO) World Congress 1999.
Barbara Levy, "Use of a New Vessel Ligation Device During Vaginal Hysterectomy" FIGO 2000, Washington, D.C..
E. David Crawford, "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Tissue"; MICCAI 2005; LNCS 3750 pp. 624-632, DATED: 2005.
Mclellan et al., "Vessel Sealing for Hemostasis During Pelvic Surgery" Int'l Federation of Gynecology and Obstetrics FIGO World Congress 2000, Washington, DC.
Mclellan et al. "Vessel Sealing for Hemostasis During Gynecologic Surgery" Sales/Product Literature 1999.
U.S. Appl. No. 08/926,869, filed Sep. 10, 1997, James G. Chandler, abandoned.
U.S. Appl. No. 09/177,950, filed Oct. 23, 1998, Randel A. Frazier, abandoned.
U.S. Appl. No. 09/387,883, filed Sep. 1, 1999, Dale F. Schmaltz, abandoned.
U.S. Appl. No. 09/591,328, filed Jun. 9, 2000 Thomas P. Ryan, abandoned.
U.S. Appl. No. 12/336,970, filed Dec. 17, 2008, Paul R. Sremeich, abandoned.
U.S. Appl. No. 13/731,674, filed Dec. 31, 2012, Wayne Siebrecht, abandoned.

* cited by examiner

ELECTRIC STAPLER DEVICE

CROSS REFERENCE TO RELATED APPLICATION

This application is a continuation application of U.S. patent application Ser. No. 15/367,868, filed on Dec. 2, 2016, now U.S. Pat. No. 10,548,658, which is a continuation application of U.S. patent application Ser. No. 14/043,039, filed on Oct. 1, 2013, now U.S. Pat. No. 9,526,564, which claims the benefit of U.S. Provisional Application No. 61/711,063, filed on Oct. 8, 2012, the entire contents of each of which are hereby incorporated herein by reference.

BACKGROUND

Technical Field

The present disclosure relates to electrosurgical instruments used for open and endoscopic surgical procedures. More particularly, the present disclosure relates to an apparatus with multi-circuit seal plates for use in simulating staples with electronic seals.

Description of Related Art

Staples have traditionally been used to replace suturing when joining or anastomosing various body structures such as, for example, the bowel or bronchus. The surgical stapling devices employed to apply these staples are generally designed to simultaneously cut and seal an extended segment of tissue in a patient, thus vastly reducing the time and risks of such procedures.

Linear or annular surgical stapling devices are employed by surgeons to sequentially or simultaneously apply one or more linear rows of surgical fasteners, e.g., staples or two-part fasteners, to body tissue for the purpose of joining segments of body tissue together and/or for the creation of an anastomosis. Linear surgical stapling devices generally include a pair of jaws or finger-like structures that otherwise encompass or engage body tissue. When the surgical stapling device is actuated and/or "fired," firing bars move longitudinally and contact staple drive members in one of the jaws, and surgical staples are pushed through the body tissue and into/against an anvil in the opposite jaw thereby crimping the staples closed. A knife blade may be provided to cut between the rows/lines of staples. Examples of such surgical stapling devices are described in U.S. Pat. Nos. 4,354,628, 5,014,899 and 5,040,715, the entirety of each of which is incorporated herein by reference.

Annular surgical stapling devices generally include an annular staple cartridge assembly including a plurality of annular rows of staples, typically two, an anvil assembly operatively associated with the annular cartridge assembly, and an annular blade disposed internal of the rows of staples. Examples of such annular surgical stapling devices are described in U.S. Pat. Nos. 5,799,857 and 5,915,616 to Robertson et al., the entirety of each of which is incorporated herein by reference.

In general, an end-to-end anastomosis stapler typically places an array of staples into the approximated sections of a patient's bowels or other tubular organs. The resulting anastomosis contains an inverted section of bowel which contains numerous "B" shaped staples to maintain a secure connection between the approximated sections of bowel.

SUMMARY

As used herein, the term "distal" refers to the portion that is being described which is further from a user, while the term "proximal" refers to the portion that is being described which is closer to a user.

As can be appreciated staples leave a foreign body in the patient necessitating a need for a surgical device that creates a similar surgical effect to a staple without leaving a staple within a patient.

According to one aspect of the present disclosure, an end effector assembly adapted to couple to an electrosurgical instrument is disclosed and includes a plurality of spaced apart small seal plates on opposing jaw members where each seal plate forms a pair of seal plates with the corresponding seal plate on the opposing jaw member. Each pair of seal plates is individually activatable, and the pair of seal plates are activated in sequence. When the opposing jaw members are in an approximated position, the pairs of seal plates around the periphery of each jaw member define a gap therebetween that is larger than the gap between pairs of seal plates along the center of each jaw member.

According to another aspect of the present disclosure, an end effector assembly of a forceps includes first and second jaw members, at least one of the jaw members moveable relative to the other between a spaced-apart position and an approximated position for grasping tissue therebetween. Each jaw member includes a plurality of spaced apart seal plates, and each seal plate corresponds to a seal plate on the opposite jaw member to form a pair of seal plates, each pair of seal plates is individually activatable. The jaw members further include a cutting element. When the first and second jaw members are in an approximated position, the pairs of seal plates closer to the cutting element define a gap therebetween that is smaller than the gap between pairs of seal plates further from the cutting element.

According to a further aspect of the present disclosure, the cutting element is located along a central axis on each jaw member.

According to another aspect of the present disclosure, each pair of seal plates receives electrical energy in a sequence.

According to a further aspect of the present disclosure, the plurality of spaced apart seal plates are each attached to an insulator plate without touching any other seal plates.

According to another aspect of the present disclosure, the end effector assembly further includes at least one orifice within the insulator plate configured to supply a clotting agent or factor and or a surgical adhesive prior to supplying electrical energy to each pair of seal plates.

According to a further aspect of the present disclosure, the end effector assembly includes a haptic feedback mechanism disposed within the forceps and configured to supply feedback to the user when each pair of seal plates receives an electrical signal.

According to another aspect of the present disclosure, an end effector assembly of a forceps includes first and second jaw members with at least one of the jaw members moveable relative to the other between a spaced-apart position and an approximated position for grasping tissue therebetween. Each jaw member includes a plurality of spaced apart seal plates, and each seal plate corresponds to a seal plate on the opposite jaw member to form a pair of seal plates. Each pair of seal plates is individually activatable. When the first and second jaw members are in the approximated position, the pairs of seal plates around the periphery of each jaw member define a gap therebetween that is larger than the gap between pairs of seal plates along the center of each jaw member.

According to another aspect of the present disclosure, the end effector assembly further includes a cutting element on at least one jaw member. The cutting element may be an electrical cutting element or a knife blade.

According to another aspect of the present disclosure, the first and second jaw members are circular in shape and are moveable relative to one another along an axis aligned through the end effector assembly to allow for end-to-end anastomosis.

According to another aspect of the present disclosure, the end effector assembly further includes at least one orifice configured to supply a seal aid to the seal plate.

According to another aspect of the present disclosure, a method for generating a plurality of electric staples includes the step of grasping a portion of tissue between a first and second jaw member. Each jaw member includes a plurality of spaced apart seal plates, and each seal plate corresponds to a seal plate on the opposite jaw member to form a pair of seal plates with the pairs of seal plates defined along the periphery of the jaw members defining a gap therebetween that is larger than the gap between the pairs of seal plates along the center of each jaw member. The method further includes the steps of sending an electrical signal to a first pair of seal plates and sending another electrical signal to a second pair of seal plates.

The method may further include the step of supplying a seal aid to at least one seal plate prior to supplying an electrical signal thereto.

Alternatively or in addition, the method may include the step of supplying an audible sound or haptic feedback when the electrical signals are sent to each pair of seal plates.

Alternatively or in addition, the plurality of spaced apart seal plates may be separated by an insulator.

Alternatively or in addition, the method may include the step of varying a seal strength by supplying an electrical signal to different pairs of seal plates, wherein the gap between at least two pairs of seal plates is different. The gap defined between the first pair of seal plates may be greater or smaller than the gap between the second pair of seal plates.

BRIEF DESCRIPTION OF THE DRAWINGS

Various embodiments of the present disclosure are described herein with reference to the drawings wherein.

DETAILED DESCRIPTION

Figure 1A:
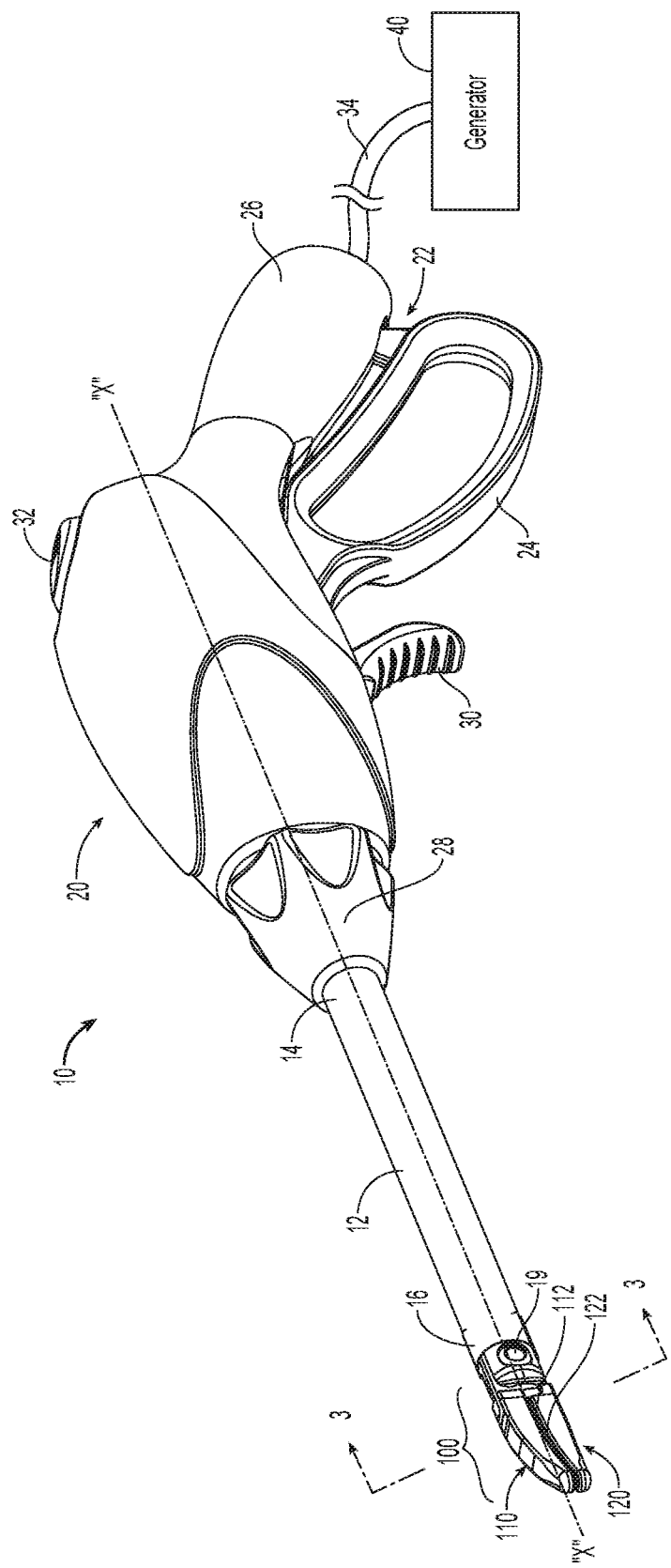
FIG. 1A is a perspective view of an endoscopic forceps having an end effector including a plurality of seal plates in accordance with an embodiment of the present disclosure.

Embodiments of the present disclosure are described in detail with reference to the drawing figures wherein like reference numerals identify similar or identical elements.

In accordance with the present disclosure, generally an end effector includes an upper seal plate and a lower seal plate described collectively as seal plates. The seal plates according to the present disclosure are manufactured to include a plurality of seal plate segments. The seal plate segments are configured to be selectively energized by a control circuit. Alternatively, two or more seal plate segments may be configured to be simultaneously energized by one or more electrical circuits. In this manner, tissue is selectively treated by one or more the individual seal plate segments or sequentially treated by one or more of the circuits that connect to the various seal plate segments. As such, the end effectors according to the present disclosure are configured and/or customized such that the tissue, or separate portions of the tissue, grasped between the jaw members, may be selectively treated.

Figure 1B:
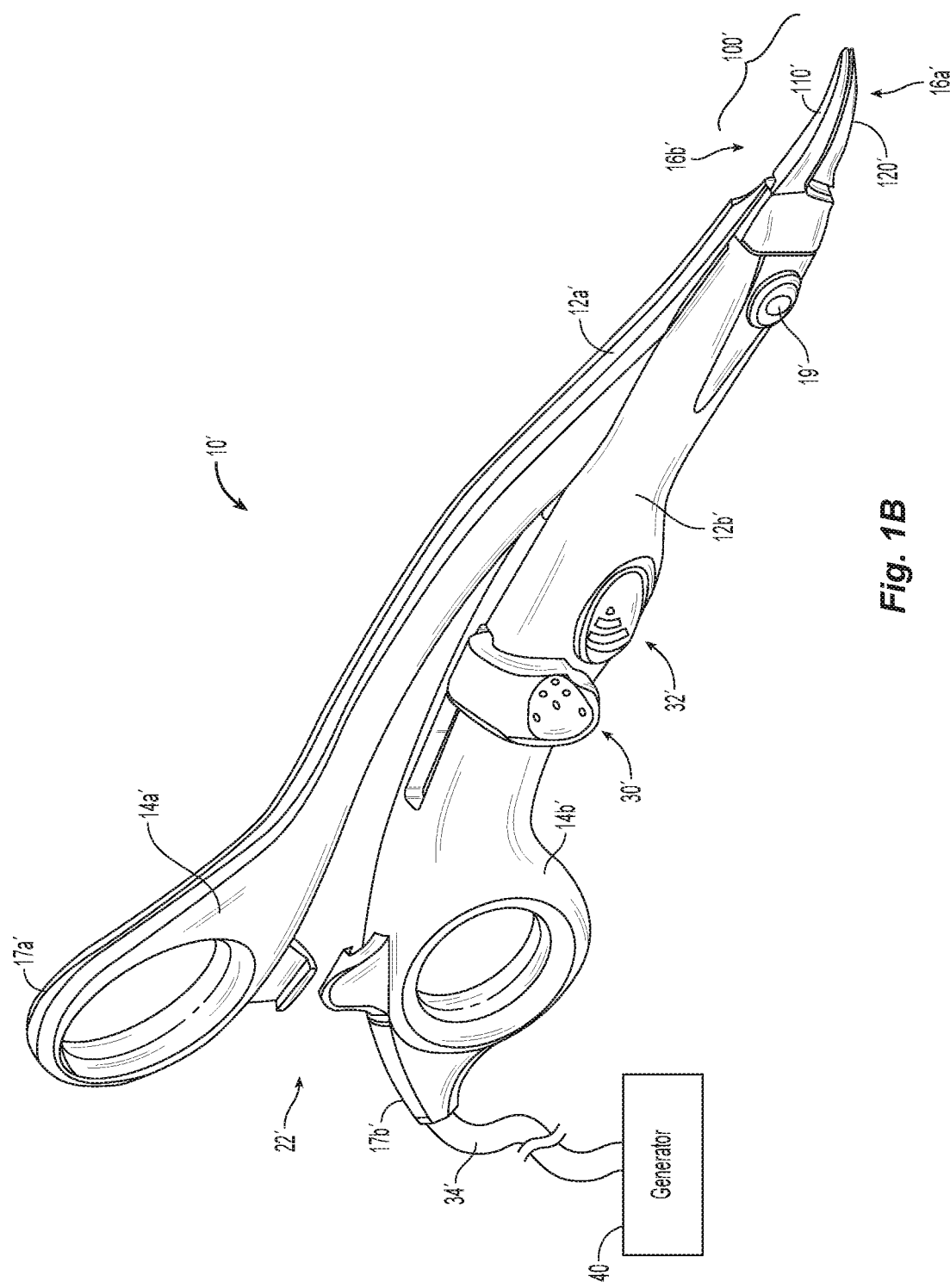
FIG. 1B is a perspective view of forceps for use in an open surgical procedure having an end effector including a plurality of seal plates in accordance with another embodiment of the present disclosure.

Referring now to the figures, FIG. 1A depicts an endoscopic forceps 10 for use in connection with endoscopic surgical procedures and FIG. 1B depicts an open forceps 10' for use in traditional open surgical procedures. For the purposes herein, either an endoscopic instrument, e.g., forceps 10, or an open surgery instrument, e.g., forceps 10', may utilize an end effector in accordance with the present disclosure. Obviously, different electrical, optical and mechanical connections and considerations may apply to each particular type of instrument, however, the novel aspects with respect to the end effector assemblies described herein and their operating characteristics remain generally consistent with respect to both the endoscopic or open surgery designs.

Turning now to FIG. 1A, the endoscopic forceps 10 is coupled to an electrosurgical generator 40, or other suitable surgical energy source. Forceps 10 is adapted to seal tissue using radiofrequency (RF) energy or other suitable electrosurgical energy including microwave, RF, ultrasonic, and light energy. For the purposes herein, the generator 40 will be described using RF energy. Generator 40 is configured to provide electrosurgical energy at any suitable RF frequency. For example, generator 40 may provide an energy signal having a frequency from about 1 MHz to about 300 GHz.

Forceps 10 is coupled to generator 40 via a cable 34. Cable 34 is configured to transmit one or more RF energy signals and/or energy control signals between the generator 40 and the forceps 10. Forceps 10 may alternatively be configured as a self-contained instrument that includes the functionality of the generator 40 within the forceps 10 (e.g., an energy source, a signal generator, a control circuit, etc.). For example, forceps 10 may include a battery (not explicitly shown) that provides electrical energy, an RF generator (40) connected to the battery and configured to generate one or more RF energy signals and a microprocessor to perform measurement and control functions and to selectively delivery one or more RF energy signals to the end effector 100.

Forceps 10 includes a housing 20, a handle assembly 22, a rotating assembly 28, a trigger assembly 30 and an end effector 100. Forceps 10 further includes a shaft 12 having a distal end 16 configured to engage the end effector 100 and a proximal end 14 configured to engage the housing 20 and/or the rotating assembly 28. Cable 34 connects to wires (not explicitly shown) in the housing 20 that extend through the housing 20, shaft 12 and terminate in the end effector 100 thereby providing one or more electrical energy signals to the upper and lower sealing plates 112, 122.

Handle assembly 22 includes a fixed handle 26 and a moveable handle 24. Fixed handle 26 is integrally associated with housing 20 and movable handle 24 is movable relative to the fixed handle 26 to actuate the end effector 100 between an open condition and a closed condition to grasp and treat tissue positioned therebetween. Rotating assembly 28 is rotatable in a clockwise and a counter-clockwise rotation to rotate end effector 100 about longitudinal axis "X-X." Housing 20 houses the internal working components of forceps 10.

End effector 100 includes upper and lower jaw members 110 and 120 each having a proximal end and a distal end, respectively. Jaw members 110 and 120 are pivotable about a pivot 19 and are movable between a first condition wherein jaw members 110 and 120 are closed and mutually cooperate to grasp, seal and/or sense tissue therebetween (See FIGS. 1A and 1B) and a second condition wherein the jaw members 110 and 120 are spaced relative to another (See FIG. 2).

Each jaw member 110, 120 includes a tissue contacting surface 112, 122, respectively, disposed on an inner-facing surface thereof. Tissue contacting surfaces 112 and 122 cooperate to grasp tissue positioned therebetween and are configured to coagulate and/or seal tissue upon application of energy from generator 40. Tissue contacting surfaces 112 and 122 may be further configured to cut tissue and/or configured to position tissue for cutting after tissue coagulation and/or tissue sealing is complete. One or more of the tissue contacting surfaces 112, 122 may form part of the electrical circuit that communicates energy through the tissue held between the upper and lower jaw members 110 and 120, respectively.

Trigger assembly 30 may be configured to actuate a knife (e.g., knife assembly 186, See FIG. 4A) disposed within forceps 10 to selectively cut/sever tissue grasped between jaw members 110 and 120 positioned in the first condition. Switch 32 is configured to selectively provide electrosurgical energy to end effector assembly 100.

Referring now to FIG. 1B, an open forceps 10' is depicted and includes end effector 100' attached to a handle assembly 22' that includes a pair of elongated shaft portions 12a' and 12b'. Each elongated shaft portion 12a', 12b' includes a respective proximal end 14a', 14b' and a distal end 16a', 16b'. The end effector assembly 100' includes upper and lower members 110', 120' formed from, or attached to, each respective distal end 16b' and 16a' of shafts 12b' and 12a'. Shafts 12a' and 12b are attached via pivot 19' and are configured to pivot relative to one another thereby actuating the jaw members 110', 120' between the first condition and the second condition, as described hereinabove.

Shafts 12a' and 12b' include respective handles 17a' and 17b' disposed at the proximal ends 14a' and 14b' thereof. Handles 17a' and 17b' facilitate scissor-like movement of the shafts 12a' and 12b' relative to each other, which, in turn, actuate the jaw members 110' and 120' between a first condition and a second condition. In the first condition, the jaws 110' and 120' are disposed in spaced relation relative to one another and, in a second condition, the jaw members 110' and 120' cooperate to grasp tissue therebetween.

In some embodiments, one or more of the shafts, e.g., shaft 12a', includes a switch assembly 32' configured to selectively provide electrical energy to the end effector assembly 100'. Forceps 10' is depicted having a cable 34' that connects the forceps 10' to generator 40 (as shown in FIG. 1). Switch assembly 32' is configured to selectively delivery the electrically energy from the generator 40 to the seal plates (not explicitly shown, see seal plates 112, 122 in FIGS. 2 and 3). Switch assembly 32' may also be configured to select the electrosurgical energy delivery mode and/or the delivery sequencing as will be discussed hereinbelow.

Trigger assembly 30' is configured to actuate a knife assembly 186, as described with respect to FIG. 2 hereinbelow, disposed within forceps 10'. The proximal end of the knife assembly 186 (See FIG. 4A) connects to trigger assembly 30' within the shaft 12b' of the forceps 10'. Knife assembly 186 extends through shaft 12b' and forms a distal cutting edge on the distal end thereof (See FIG. 4A). Knife assembly 186, when actuated by trigger assembly 30', extends the distal cutting edge distally through a knife channel 115 (see FIG. 4A) to sever tissue positioned between the jaw members 110' and 120'.

Figure 2:
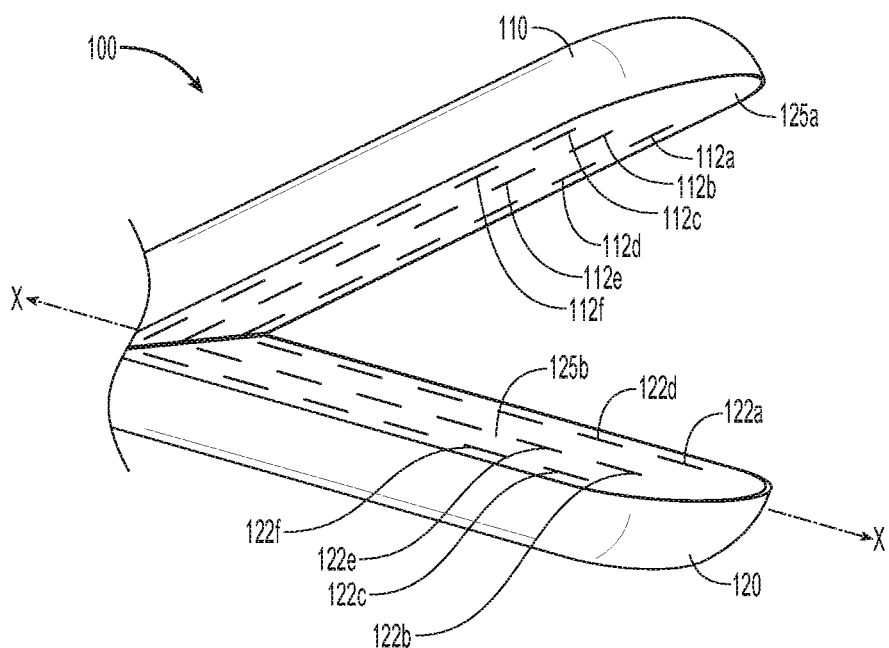
FIG. 2 is a perspective view of the end effector for use with the forceps of FIG. 1A and FIG. 1B in an open condition and including a plurality of seal plates.

With reference to FIG. 2, each seal plate 112, 122 forms a planar sealing surface that includes a plurality of seal plate segments 112a-112f and 122a-122f, respectively, electrically isolated from each other by insulating members 125a, 125b. Each seal plate segment 112a-112f on the top jaw 110 has an opposing seal plate segment 122a-122f on the bottom jaw 120 that form each pair of seal plate segments (pair of electrodes). Each seal plate segment 112a-112f and 122a-122f forms a substantially equal portion of the planar sealing surface, however the thickness of each seal plate segment may vary (See FIG. 3). The number of seal plates segments 112a-112f, 122a-122f on the jaw members may vary as with the number of seal plate segments along axis "X-X" and perpendicular to axis "X-X."

Insulating members 125a and 125b may be formed from any suitable insulating material or dielectric material that provides electrical isolation between the seal plate segments 112a-112f and 122a-122f. Insulating members 125a and 125b may be formed from a polytetrafluorethylene (PTFE), polypropylene, polychlorotrifluoroethylene (IPCTFE), polyethylene, polyethyleneterephthalate (PET), polyvinylchloride (PVC), a ceramic material or even air in a gap formed between adjacent seal segments. The insulating members 125a and 125b provide areas grasped within the end effector 100 that are not sealed and therefore receive less tissue damage to allow the body to generate the remainder of the seal with healthy tissue.

The individual seal plate segments 112a-112f and 122a-122f may be pre-selected, or dynamically selected, as part of one or more electrical circuits that deliver electrosurgical energy to tissue positioned between the jaw members 110 and 120. For example, in one configuration the end effector 100 may include a first bipolar circuit that includes the inner seal plate segments 112a and 122a, a second bipolar circuit that includes the middle seal plate segments 112b and 122b and a third bipolar circuit that includes the outer seal plate segments 112c and 122c wherein the first, second and third bipolar circuits are independently enabled and/or controlled to deliver electrosurgical energy to tissue.

The seal plate segments on each jaw (e.g., lower seal plate segments 122a-122f on lower jaw 120) are arranged such that the seal plate segments are positioned in rows and columns. The number of rows and columns can be varied to control the number of individual seals caused by a single grasp of tissue by the end effector 100. The seal plate segments 112a-112f on the upper seal plate 112 may have corresponding seal plate segments 122a-122f on the lower seal plate 122 positioned oppose and one another, as illustrated in FIGS. 2 and 3.

Figure 3:
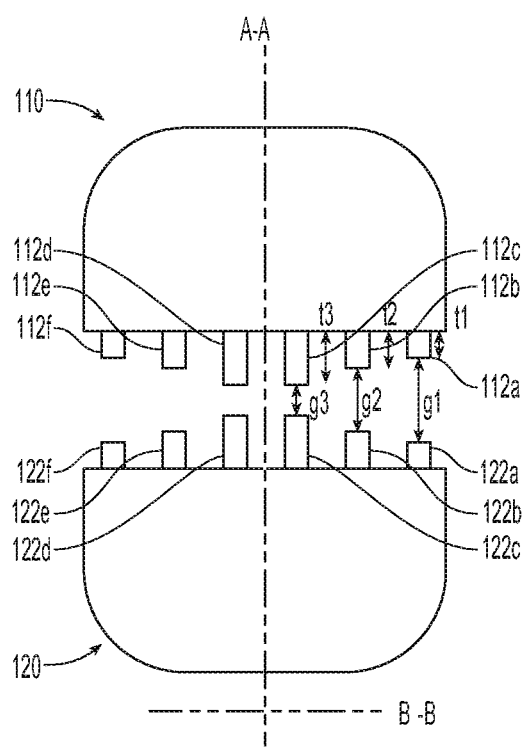
FIG. 3 is a front, cross-sectional view of the end effector of FIG. 2 in a closed condition.

With reference to FIG. 3, the seal segments 112a-112f and 122a-122f are arranged such that the seal segments 112c-112d and 122c-122d closest to the central axis "A-A" have a greater thickness t3. Also, when jaws 110 and 120 are in the closed position, the gap g3 between segments 112d and 122d, and similarly between segments 112c and 122c is the smallest. This creates the tightest seal in the center or closest to the cut if there is a knife blade 184 (see FIG. 4B) (or electrical cutter 610) along the central axis "A-A." The smallest gap g3 creates the highest compression seal which limits the acute bleeding. More specifically, the seal in the center may be about 3.5 to about 4.5 times systolic pressure, although the desired pressure range may vary depending on tissue type or other factors. As you move left or right along Axis B-B from the central axis "A-A" the thickness of the seal segments 112e-112f, 112b-112a, 122e-122f, and 122b-122a is smaller. In other words the thickness t2 of 112e is greater than the thickness t1 of 112f Therefore, when the jaws 110, 120 are in a closed position, the gap increases as you move left or right away from the central axis "A-A" along axis "B-B." In other words the gap g2 between 112b and 122b is smaller than the gap g1 between 112a and 122a, and therefore the seal in the middle may be about 2.5 to 3.5 times systolic pressure at each seal. The medium gap g2 allows for medium compression of tissue. The larger gap g1 allows for a lower compression which reduces tissue damage. The largest gap seal allows for about 1.5 to about 2.5 times systolic pressure at each seal although, similarly as noted above, the desired pressure range may vary depending on tissue type or other factors.

Figure 4A:
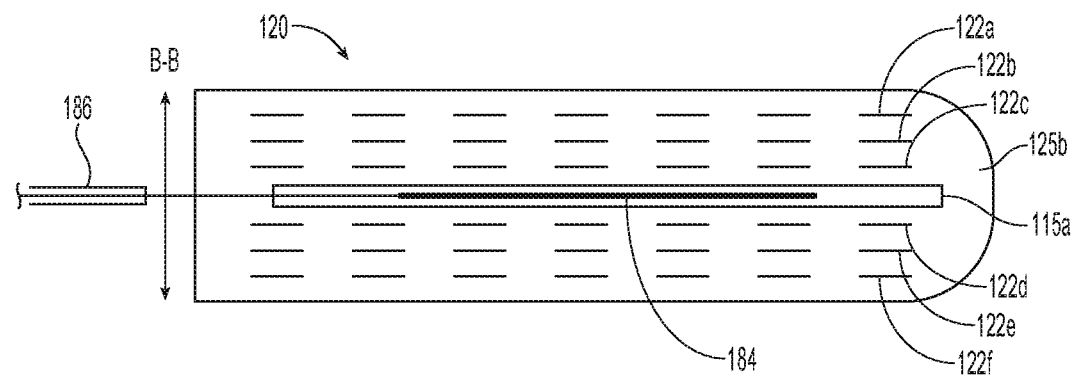
FIGS. 4A and 4B are top views of lower jaw member and upper jaw member, respectively in accordance with another embodiment of the present disclosure.
Figure 4B:
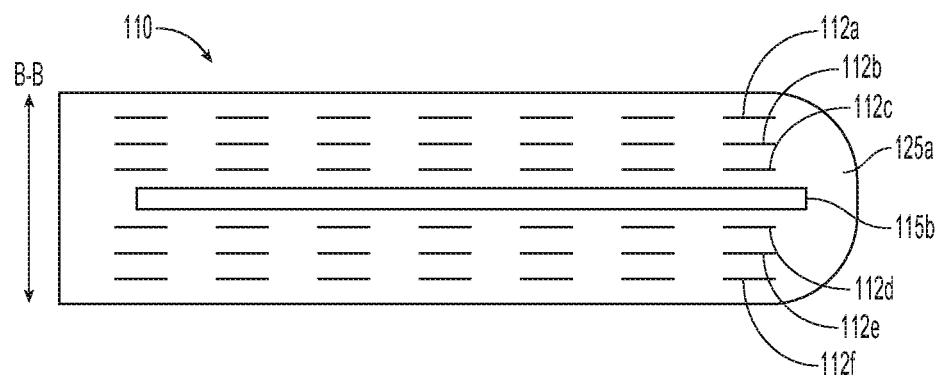

With reference to FIGS. 4A and 4B, knife channel 115 is defined by a channel formed within one or both jaw members 110 and 120 to permit reciprocation of knife assembly 186 therethrough, e.g., via activation of the trigger assembly 30, 30' (See FIGS. 1A and 1B). The upper jaw member 110 and the lower jaw member 120, while in a closed position form a knife channel 115 therebetween. Knife channel 115 includes an upper knife channel 115b, formed in the upper jaw member 110, mated with a lower knife channel 115a, formed in the lower jaw member 120.

Alternatively, instead of a knife blade assembly 186, the end effector 100 may include an electrical cutting electrode 610 (See FIG. 6B) on the lower 110 and/or upper jaw member 120.

Figure 6A:
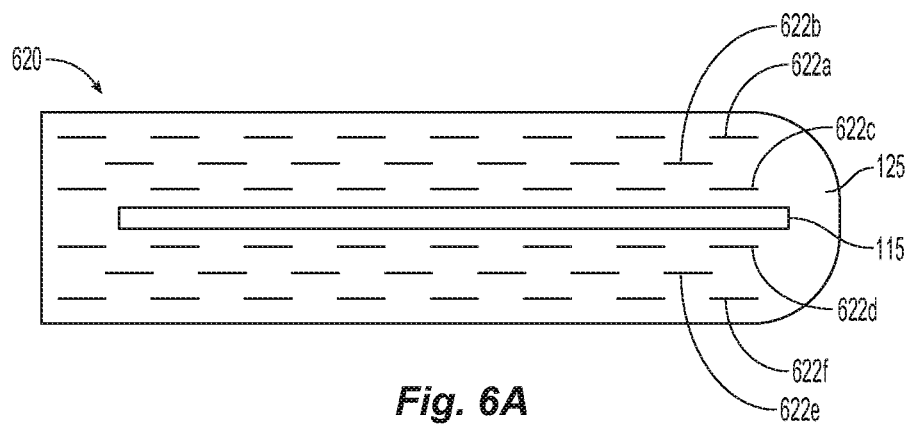
FIGS. 6A-6C are top views of a jaw member in accordance with alternate embodiments of the present disclosure.
Figure 6B:
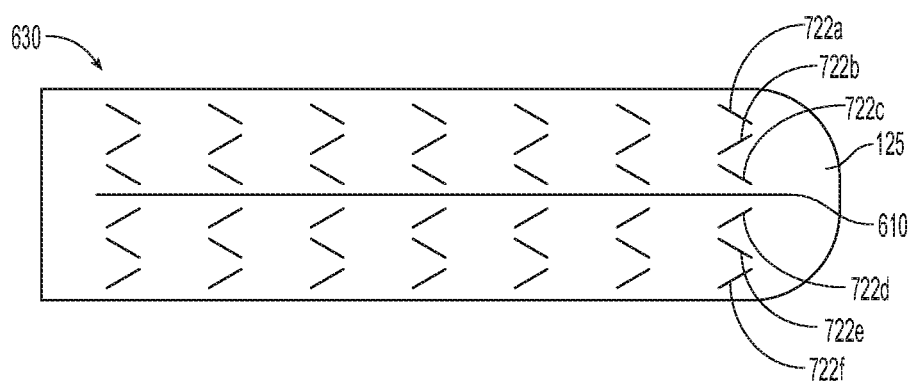

The seal segments 122a-122f and 112a-112f decrease in thickness as the distance increases from the knife channel 115 or electrical cutter 610 (see FIG. 6B). This allows for greatest compression closest to the knife blade 184 or the electrical cutter 610, which creates the tightest seal to prevent acute bleeding. The lowest compression is formed with the seal segments 122a, 112a, 122f, and 112f furthest from the knife channel 115 or electrical cutter 610, which allows for more blood profusion between the seal plates 122a, 112a, 122f, and 112f to allow the patient's body to slowly generate a long term seal. The number of seal segments 112a-112f and 122a-122f may vary and therefore the gradient of compression applied between each seal segment can vary.

Figure 5:
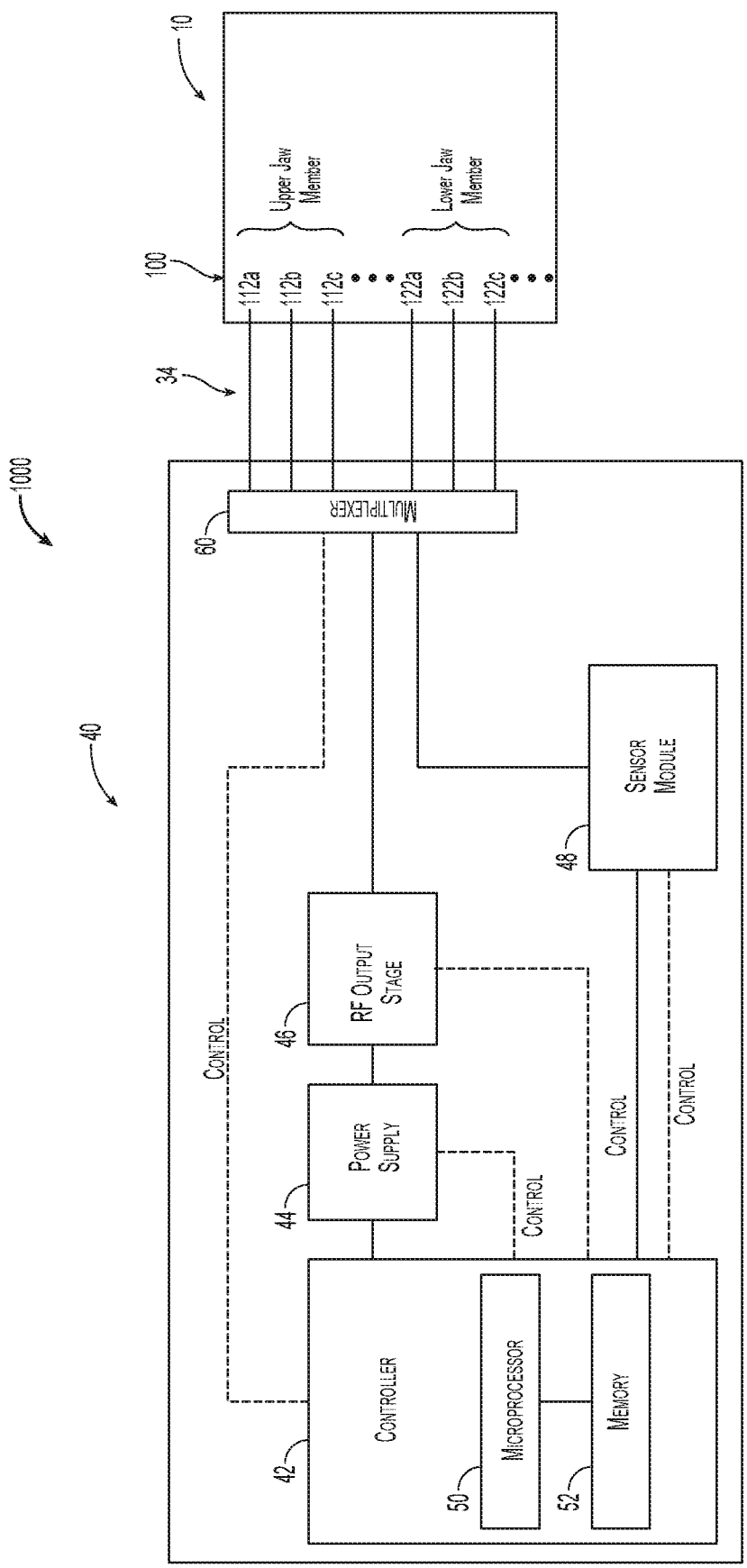
FIG. 5 is a schematic block diagram of an electrosurgical system for use with an end effector including a plurality of seal plates according to an embodiment of the present disclosure.

Turning now to FIG. 5, a system schematic block diagram for driving an end effector 100 according to the present disclosure is indicated as system 1000. System 1000 includes a generator 40, a forceps 10 with a multi-seal circuit end effector 100 connected by a cable 34. The generator 40 includes a controller 42, a power supply 44, an RF output stage 46, a sensor module 48 and a multiplexer 60. The power supply 44 provides DC power to the RF output stage 46 that converts the DC power into one or more RF energy signals. The one or more RF energy signals are individually provided to the multiplexer 60.

The controller 42 includes a microprocessor 50 having a memory 52 which may be volatile type memory (e.g., RAM) and/or non-volatile type memory (e.g., flash media, disk media, etc.). The microprocessor 50 includes a connection to the power supply 44 and/or RF output stage 46 that allows the microprocessor 50 to control the output of the generator 40 according to an open-loop and/or closed-loop control scheme. The power supply 44, RF output stage 46, multiplexer 60 and sensor module 48 are connected to, and controlled by, the controller 42 and configured to operate in concert to perform a selected surgical procedure.

For example, controller 42 may instruct the multiplexer 60 to connect an RF energy signal generated by the RF output stage 46 between any two or more segments of the end effector 100. For example, multiplexer 60 may be instructed by the controller 42 to form an electrosurgical energy delivery circuit between with seal plate 112a on the upper jaw member 110 and the seal plate 122a on the lower jaw member 120 (See FIG. 2). Additionally, controller 42 may instruct the multiplexer 60 to connect the sensor module 48 between any two or more segments of the end effector 100 and controller 42 may instruct the sensor module 48 to perform a measurement between the selected segments of the end effector 100. For example, multiplexer 60 may be instructed by the controller 42 to form a measurement circuit between the seal plate segment 112b on the upper jaw member 110 and the seal plate segment 122b on the lower jaw member 120 (See FIG. 2). Controller 42 may issue instructions to the various components in the generator 40 to performed energy delivery and measurements sequentially or simultaneously.

Controller 42, in executing a closed-loop control scheme, may instruct the multiplexer 60 to simultaneously connect two segments on the end effector 100 to the RF output stage 46 for delivery of electrosurgical energy and may further instruct the multiplexer to connect the sensor module 48 to two segments on the end effector 100 wherein the sensor module 48 provides feedback to the controller 42 for an energy delivery control loop (e.g., the sensor module 48 includes one or more sensing mechanisms/circuits for sensing various tissue parameters such as tissue impedance, tissue temperature, output current and/or voltage, etc.). The controller 42, using the energy delivery control loop, signals the power supply 44 and/or RF output stage 46 to adjust the electrosurgical energy signal.

The controller 42 also receives input signals from the input controls of the generator 40 and/or forceps 10, 10'. The controller 42 utilizes the input signals to generate instructions for the various components in the generator 40, to adjust the power output of the generator 40 and/or to perform other control functions. The controller 42 may include analog and/or logic circuitry for processing input signals and/or control signals sent to the generator 40, rather than, or in combination with, the microprocessor 50.

The microprocessor 50 is capable of executing software instructions for processing data received by the sensor module 48, and for outputting control signals to the generator 40, accordingly. The software instructions, which are executable by the controller 42, are stored in the memory 52 of the controller 42.

The sensor module 48 may also include a plurality of sensors (not explicitly shown) strategically located for sensing various properties or conditions, e.g., tissue impedance, voltage (e.g., voltage at the generator 40 and/or voltage at the tissue site) current (e.g., current at the generator 40 and/or current delivered at the tissue site, etc.) The sensors are provided with leads (or wireless) for transmitting information or signals to the controller 42. The sensor module 48 may include control circuitry that receives information and/or signals from multiple sensors and provides the information and/or signals, and/or the source of the information (e.g., the particular sensor providing the information), to the controller 42.

The sensor module 48 may include a real-time voltage sensing system and a real-time current sensing system for sensing real-time values related to applied voltage and current at the surgical site. Additionally, an RMS voltage sensing system and an RMS current sensing system may be included for sensing and deriving RMS values for applied voltage and current at the surgical site.

The generator 40 includes suitable input controls (e.g., buttons, activators, switches, touch screen, etc.) for controlling the generator 40, as well as one or more display screens for providing the surgeon with information (e.g., intensity settings, treatment complete indicators, etc.). The controls allow the surgeon to adjust power of the RF energy, waveform, and other parameters to achieve the desired waveform suitable for a particular task (e.g., surgical procedure such as tissue ablation, coagulation, cauterization, resection or any combination thereof). Further, the forceps 10, 10' may include one or more input controls, some of which may be redundant, with certain input controls included in the generator 40. Placing select input controls at the instrument 10, 10' allows for easier and faster modification of RF energy parameters during the surgical procedure without requiring interaction with the generator 40.

Returning to FIG. 2, the control circuit (e.g., controller 42) may be configured to dynamically select one or more of the seal plate segments 112a-112c and 122a-122c before and/or during the surgical procedure and may be configured to dynamically switch the selected seal plate segments that form one or more of the electrosurgical energy delivery circuits. More specifically, the control circuit (e.g., controller 42) may be configured to provide electrosurgical energy to the first bipolar circuit during a simulated stapling action, configured to provide electrosurgical energy to the second bipolar circuit during a second simulated stapling action and configured to provide electrosurgical energy to the third bipolar circuit during a third simulated stapling action. In operation, the controller 42 instructs the multiplexer 60 to direct an RF energy signal, generated by the RF output stage 46, to each of the first, second, etc. bipolar circuits during the simulated stapling actions. The simulated stapling actions may be executed consecutively, simultaneously, sequentially, or any portion of a simulated stapling action may overlap any other treatment simulated stapling action.

As each simulated stapling action is performed by the generator 40 sending an electrical signal to a pair of seal plates, for example 122a and 112a, the generator 40 may provide a ratcheting sound through a speaker (not shown) in the generator 40 or the hand held device 10 or 10'. Alternatively, the generator 40 may provide haptic feedback through a haptic mechanism (not shown) in the hand held device 10 or 10' when a signal is sent to the pair of seal plates, for example 122a and 112a, similar to feedback felt when using a traditional stapling end effector.

Figure 6C:
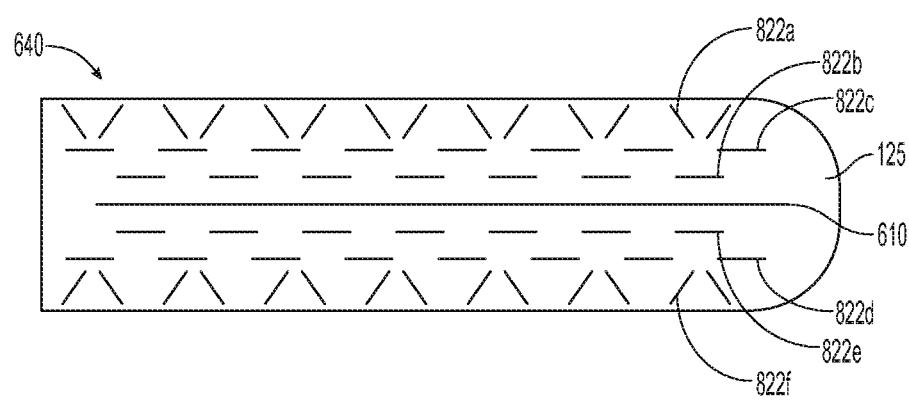

Referring now to FIGS. 6A-6C, which show different embodiments of seal plate segments that may be generated along each jaw member 110 and/or 120. FIG. 6A shows a jaw member 620 with staggered seal plate segments 622a-622f. Between each seal segment is an insulative material 125. The insulative material provides an area of unsealed tissue between each seal similar to how traditional staples form seals. FIG. 6B shows a jaw member 630 with diagonal seal segments 722a-722f. FIG. 6C shows a jaw member 640 with diagonal seal segments 822a and 822f, and staggered seal plate segments 822b-822e. Only one jaw member is shown in FIGS. 6A-6C, however, the opposite jaw member would have a similar look to the jaw member shown so that each seal plate segment forms a seal plate segment pair with the opposite seal plate segment on the opposing jaw member. The different possible arrangements of seal plate segments 622a-622f, 722a-722f, and 822a-822f allow for different seal strengths. Additionally, the thickness of the seal plate segments 612a-612f varies similar to seal plate segments 112a-112f and 122a-122f shown in FIG. 3.

Figure 7A:
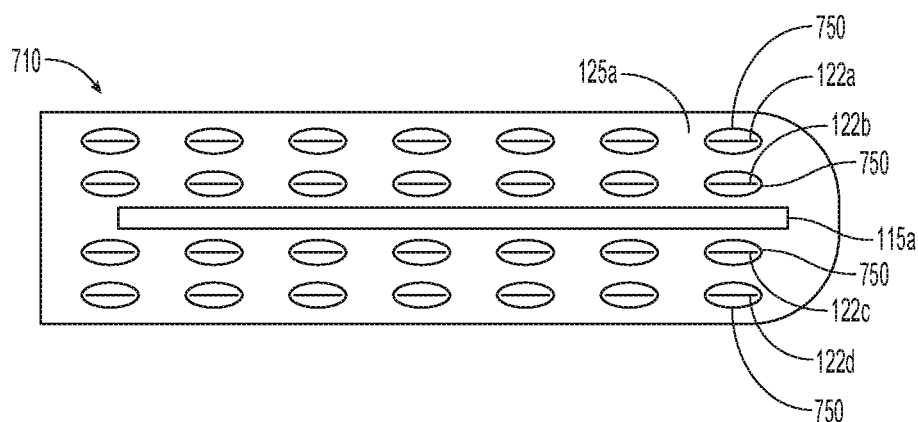
FIGS. 7A-7C are top views of a jaw member in accordance with alternate embodiments of the present disclosure.
Figure 7B:
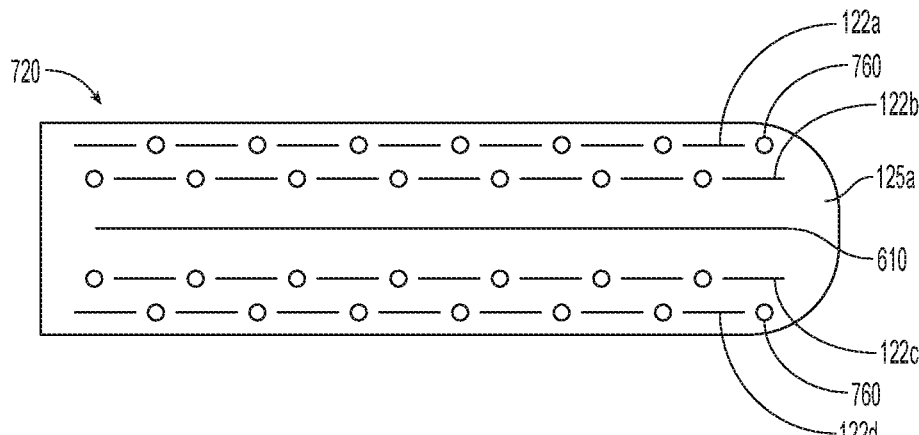
Figure 7C:
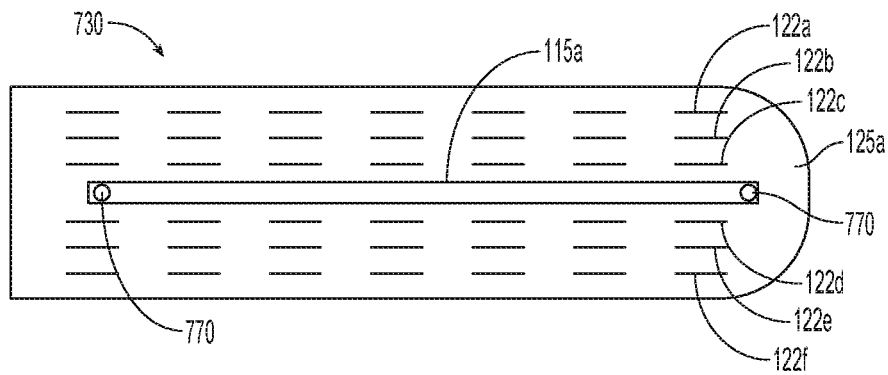

Referring to FIGS. 7A-7D, the end effector 100 may provide seal aid as the seal is generated. The seal aid may include a clotting factor, such as Fibrin, and or adhesive. FIG. 7A shows one embodiment that includes orifice rings 750 around each seal segment 122a-122d. Such that as each seal segment is activated, the seal aid is delivered through the jaw member 710 to reduce bleeding or "oozing." Alternatively, as shown in FIG. 7B, the jaw member 720 may include orifices 760 between each seal segment 122a-122d. Both jaw member 710 and 720 allow for the use of an electrical cutter 610 because the orifices 750 or 760 are around or near the seal segments 122a-122d. FIG. 7C shows another alternative for supplying seal aid near the seal that allows the seal aid to ooze from the knife channel 115 or through specific orifices 770 in the knife channel 115. Another alternative, is to have the seal aid applied directly to each seal plate segment and as each seal plate segment heats up when receiving the electrical energy the seal aid is applied to the seal.

Figure 7D:
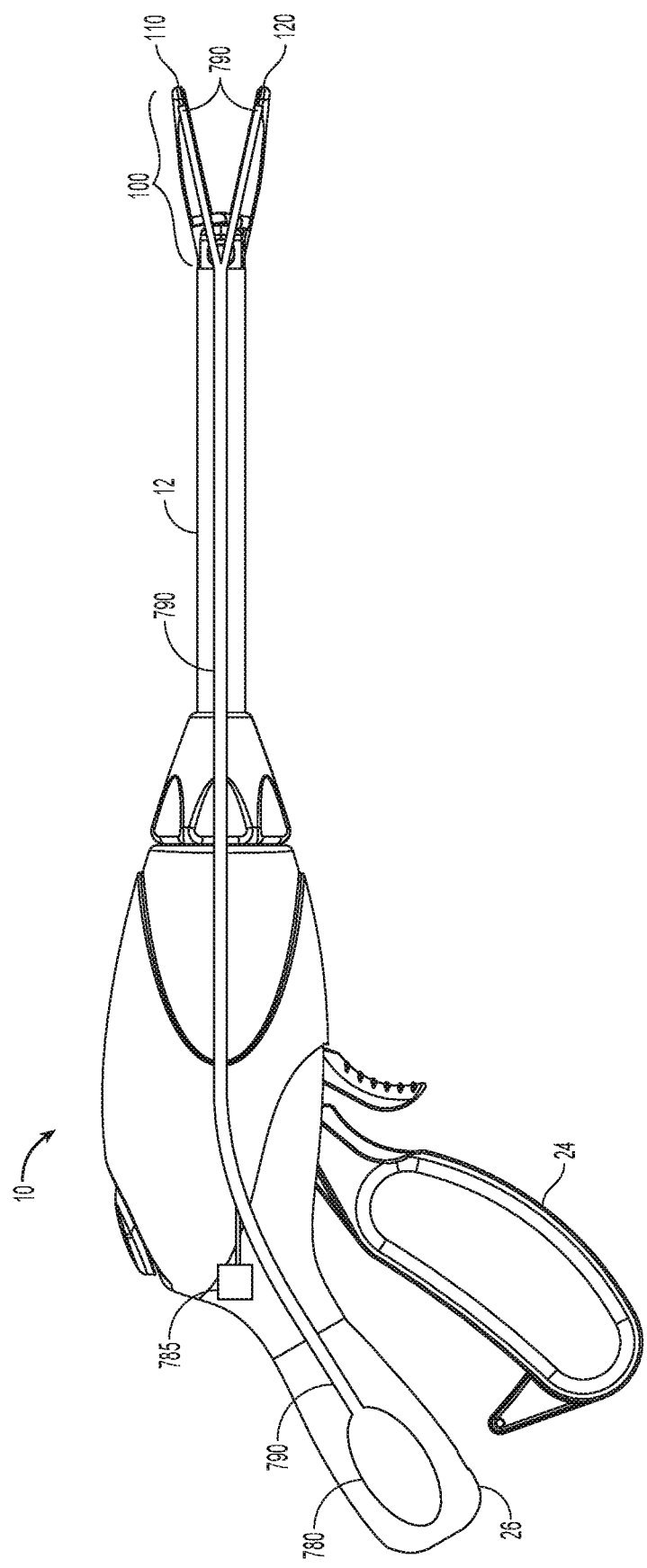
FIG. 7D is a perspective view of an endoscopic forceps having a jaw member from FIGS. 7A-7C in accordance with an embodiment of the present disclosure.

FIG. 7D shows a surgical device 10 that includes a container 780 for storing pressurized seal aid that is supplied when trigger 785 is selected by the user. The pressurized seal aid is supplied to one or more jaw members 110 and or 120 through lumen 790. The seal aid then applies to the seal through orifices 750, 760, or 770 from lumen 790.

End effector 100 may also include a lumen (not shown) that receives a cooling liquid from the surgical device 10. The cooling liquid assists in reducing tissue damage near each activated seal plate segment 122a-122f or 112a-112f by reducing the temperature of end effector 100, and therefore reducing tissue damage near each seal plate segment because the insulative material 125 remains at lower temperature.

Figure 8:
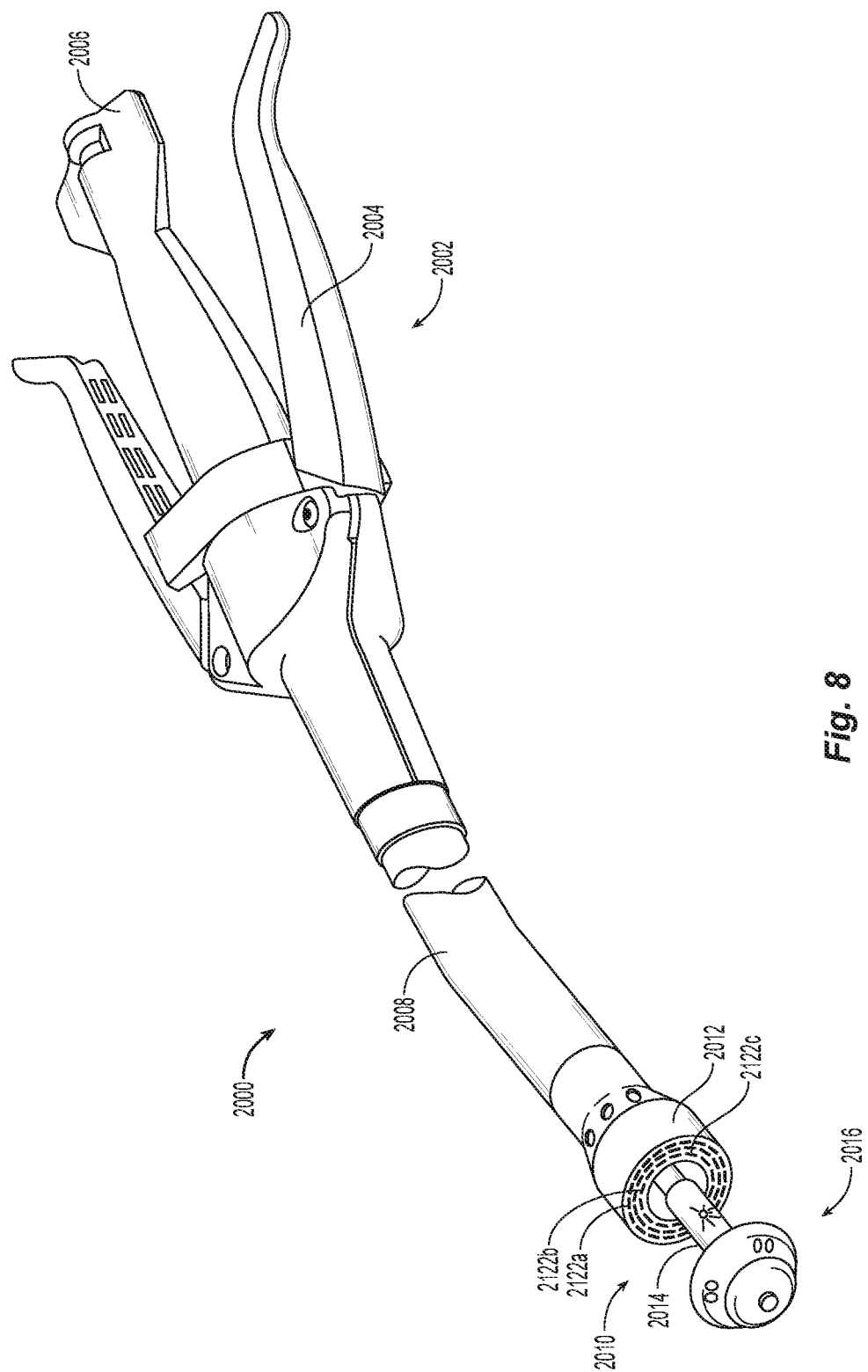
FIG. 8 illustrates an end-to-end anastomosis device for use with an alternate embodiment of the electrosurgical stapler device according to the present disclosure.

Surgical device 10 may be adapted for use as an end-to-end anastomosis (EEA) apparatus 2000 (FIG. 8), such as that disclosed in U.S. Pat. No. 7,455,676, the contents of which are hereby incorporated by reference herein in its entirety. The EEA apparatus 2000 includes a handle assembly 2002 having at least one pivotable actuating handle member 2004, and advancing means 2006. Extending from handle assembly 2002, there is provided a tubular body portion 2008 that terminates in a fastener ejection (tool) assembly 2010 having a first circular electrical stapler member 2012 that includes a plurality of seal segments 2122a-2122c in a circular pattern. The seal plate segments 2122a-2122c are located on both the first circular electrical stapler member 2012 and a second circular electrical stapler member 2016. The first and second circular electrical stapler members 2012, 2016 are connected together through shaft 2014.

When the first and second circular electrical stapler members 2012, 2016 are in a closed position, the seal plate segments 2122a-2122c are each paired with an opposing seal segment on the opposite circular electrical stapler member. The smallest gap is formed between the pair of seal segments 2122c on the inner most ring the first and second circular electrical stapler members 2012, 2016. The smallest gap allows for the most compression and therefore the "tightest" or highest quality or acute seal. The middle row of seal segments 2122b provides a slightly larger gap and a medium amount of compression. The gap is the largest between seal segments 2122a in the outer most ring, which provides the lowest compression and allows for the least "tightest" seal. In alternative embodiments the number of rings of segments may vary and therefore the varying gap/compression will vary too.

Figure 9:
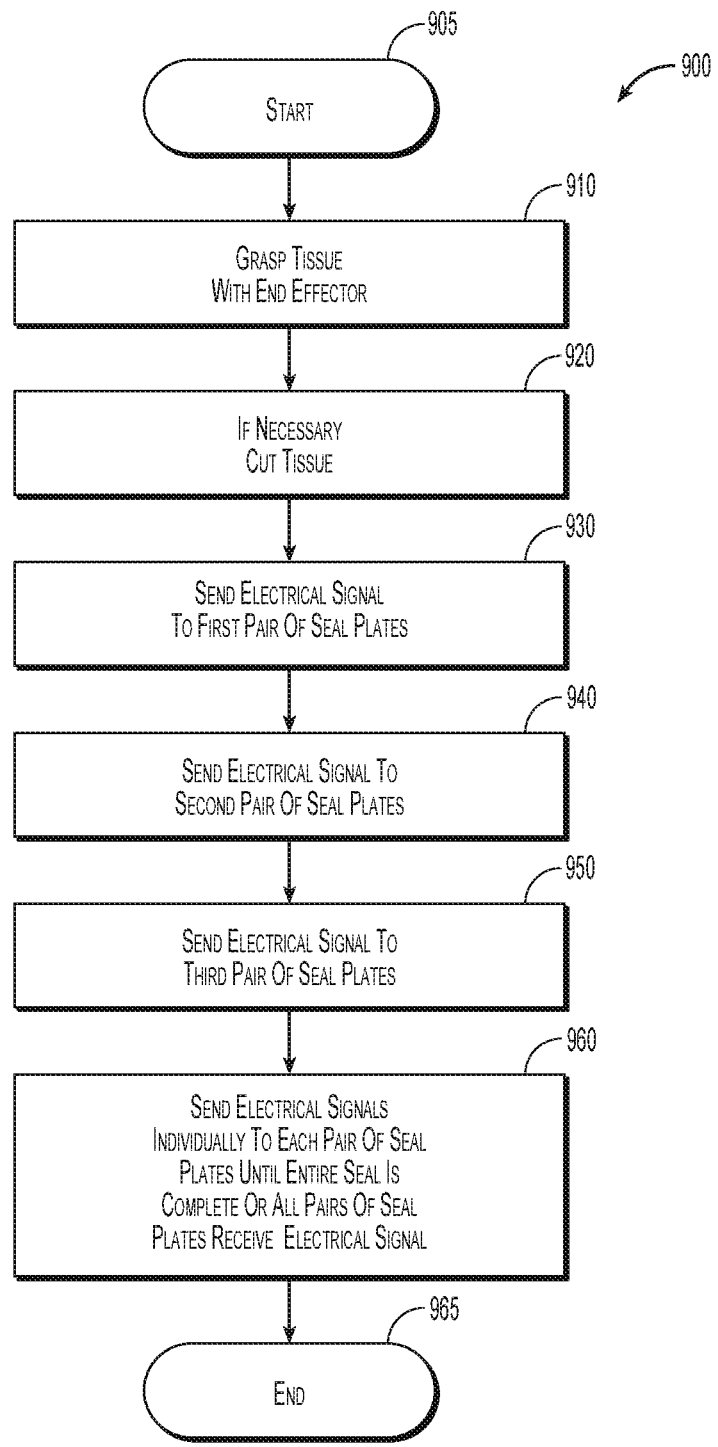
FIG. 9 is a flow chart for generating a plurality of electrosurgical staples in accordance with the present disclosure.

FIG. 9 discloses a flow chart for using an electronic stapler device 10, 10', 2000 to simulate staples during a surgical procedure. The process 900 starts at step 905 and at step 910, the surgeon grasps tissue with end effector 100. Next at step 920, the surgeon cuts the tissue if necessary using a knife blade 184 or electrical cutter 610. Alternatively, the tissue may be cut between two seals. Then at step 930, the generator 40 sends an electrical signal to a first electrode pair after the surgeon hits a trigger button on the electronic stapler device 10. Whenever the signal is sent from the generator 40, the generator 40 may provide a ratcheting sound or haptic feedback to inform the surgeon that a signal was sent and that a electric staple seal was formed. The first electrode pair may create the "tightest" or highest quality, or acute seal, i.e. between 122c and 112c (see FIG. 3), to create an acute seal first. Then at step 940, an electrical signal is sent to the a second electrode pair, i.e. between 112b and 122b, to create a medium "tight" seal. Then at 950, an electrical signal is sent to a third electrode pair, i.e. between 112a and 122a, to create the least "tightest" seal.

Alternatively, the first electrode pair may create the least "tightest" seal, i.e. between 122a and 112a (see FIG. 3), which pushes inward any blood or other fluids directionally during sealing and controls profusion of fluids at the time of sealing. The second electrode, i.e. between 112b and 122b, receives the second electrical signal to create a medium "tight" seal. Then, the third electrode pair, i.e. between 112c and 122c, receives the electrical signal to create the "tightest" seal (higher quality or acute seal).

In another alternative embodiment, the sequence may sequentially send an individual signal to each seal plate pair that generates an acute seal. Then, the sequence may sequentially send an individual signal to each seal plate pair that generates a medium "tight" seal. Finally, the sequence may sequentially send an individual signal to each seal plate pair that generates the least "tightest" seal.

The process 900 ends at step 965, when each electrode pair has been individually fired on the end effector 100 or the seal is complete at step 960. Additionally, as each pair of seal plate segments receives an electrical signal, the surgeon may select to supply a seal aid to the seal. Also, the end effector 100 may also include a cooling liquid supplied through lumens to cool the end effector 100 and reduce damage to tissue near a seal from the end effector 100 being too hot.

In alternative embodiments, more than one seal plate segment 112a-112f and 122a-122f may receive an electrical signal at the same time, however the goal is to reduce tissue damage to tissue near an energized seal plate segment by reducing the heat dissipated to the non-sealed tissue.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly of an electrosurgical instrument, comprising:
   first and second opposing jaw members, at least one of the first or second jaw members movable relative to the other of the first or second jaw members between a first position and a second position for grasping tissue therebetween, each of the first and second jaw members including:
      an insulative surface, wherein the insulative surfaces of the first and second jaw members oppose one another and are configured to facilitate grasping tissue between the first and second jaw members in the second position; and
      a plurality of seal plates protruding above the insulative surface and spaced-apart from one another to expose portions of the insulative surface therebetween, each seal plate of the plurality of seal plates configured to connect to a source of electrical energy and correspondingly pair with a seal plate of the plurality of seal plates on the opposing jaw member to form a plurality of pairs of seal plates, each pair of seal plates of the plurality of pairs of seal plates selectively energizable to conduct electrical energy therebetween independently of at least one other pair of seal plates of the plurality of pairs of seal plates,
   wherein, in the second position, the seal plates of each pair of seal plates of the plurality of pairs of seal plates define a gap therebetween, and
   wherein the gap defined between the seal plates of at least one pair of seal plates of the plurality of pairs of seal plates is different from the gap defined between the seal plates of at least one other pair of seal plates of the plurality of pairs of seal plates.

2. The end effector assembly according to claim 1, further including a cutting element located along a central axis of at least one of the first or second jaw members.

3. The end effector assembly according to claim 2, wherein the cutting element is a mechanical knife blade configured to reciprocate along the central axis.

4. The end effector assembly according to claim 2, wherein the cutting element is an energizable cutting electrode.

5. The end effector assembly according to claim 1, further including a plurality of bipolar circuits, each bipolar circuit configured to supply electrical energy to at least one pair of seal plates of the plurality of pairs of seal plates.

6. The end effector assembly according to claim 5, wherein each pair of seal plates of the plurality of pairs of seal plates corresponds to one bipolar circuit of the plurality of bipolar circuits.

7. The end effector assembly according to claim 1, wherein each pair of seal plates is individually energizable.

8. The end effector assembly according to claim 1, wherein at least two pairs of seal plates of the plurality of pairs of seal plates are energizable in a sequence.

9. The end effector assembly according to claim 1, wherein, in the second position, each pair of seal plates of the plurality of pairs of seal plates applies a force to tissue grasped between the first and second jaw members, and wherein at least one pair of seal plates of the plurality of pairs of seal plates applies a force greater than a force applied by at least one other pair of seal plates of the plurality of pairs of seal plates.

10. The end effector assembly according to claim 9, wherein the seal plates of the at least one pair of seal plates of the plurality of pairs of seal plates define a gap therebetween in the second position that is different from a gap defined between the seal plates of the at least one other pair of seal plates of the plurality of pairs of seal plates, and wherein the different gaps at least partially account for the different forces.

11. The end effector assembly according to claim 1, wherein at least one pair of seal plates of the plurality of pairs of seal plates is configured to enable measurement of at least one parameter independently of parameter measurement enabled by at least one other pair of seal plates of the plurality of pairs of seal plates.

12. The end effector assembly according to claim 11, wherein the at least one parameter includes at least one of impedance, temperature, current, or voltage.

13. The end effector assembly according to claim 12, wherein energization of the at least one pair of seal plates of the plurality of pairs of seal plates is controllable based upon the at least one measured parameter independently of control of energization of the at least one other pair of seal plates of the plurality of pairs of seal plates.

14. An end effector assembly of an electrosurgical instrument, comprising:
- first and second opposing jaw members, at least one of the first or second jaw members movable relative to the other of the first or second jaw members between a first position and a second position for grasping tissue therebetween, each of the first and second jaw members including:
- an insulative surface, wherein the insulative surfaces of the first and second jaw members oppose one another and are configured to facilitate grasping tissue between the first and second jaw members in the second position; and
- a plurality of seal plates protruding above the insulative surface and spaced-apart from one another to expose portions of the insulative surface therebetween, each seal plate of the plurality of seal plates configured to connect to a source of electrical energy and correspondingly pair with a seal plate of the plurality of seal plates on the opposing jaw member to form a plurality of pairs of seal plates, each pair of seal plates of the plurality of pairs of seal plates selectively energizable to conduct electrical energy therebetween independently of at least one other pair of seal plates of the plurality of pairs of seal plates,
- wherein, in the second position, each pair of seal plates of the plurality of pairs of seal plates applies a force to tissue grasped between the first and second jaw members, and wherein at least one pair of seal plates of the plurality of pairs of seal plates applies a force greater than a force applied by at least one other pair of seal plates of the plurality of pairs of seal plates.

15. The end effector assembly according to claim 14, wherein the seal plates of the at least one pair of seal plates of the plurality of pairs of seal plates define a gap therebetween in the second position that is different from a gap defined between the seal plates of the at least one other pair of seal plates of the plurality of pairs of seal plates, and wherein the different gaps at least partially account for the different forces.

* * * * *